Figure 1:
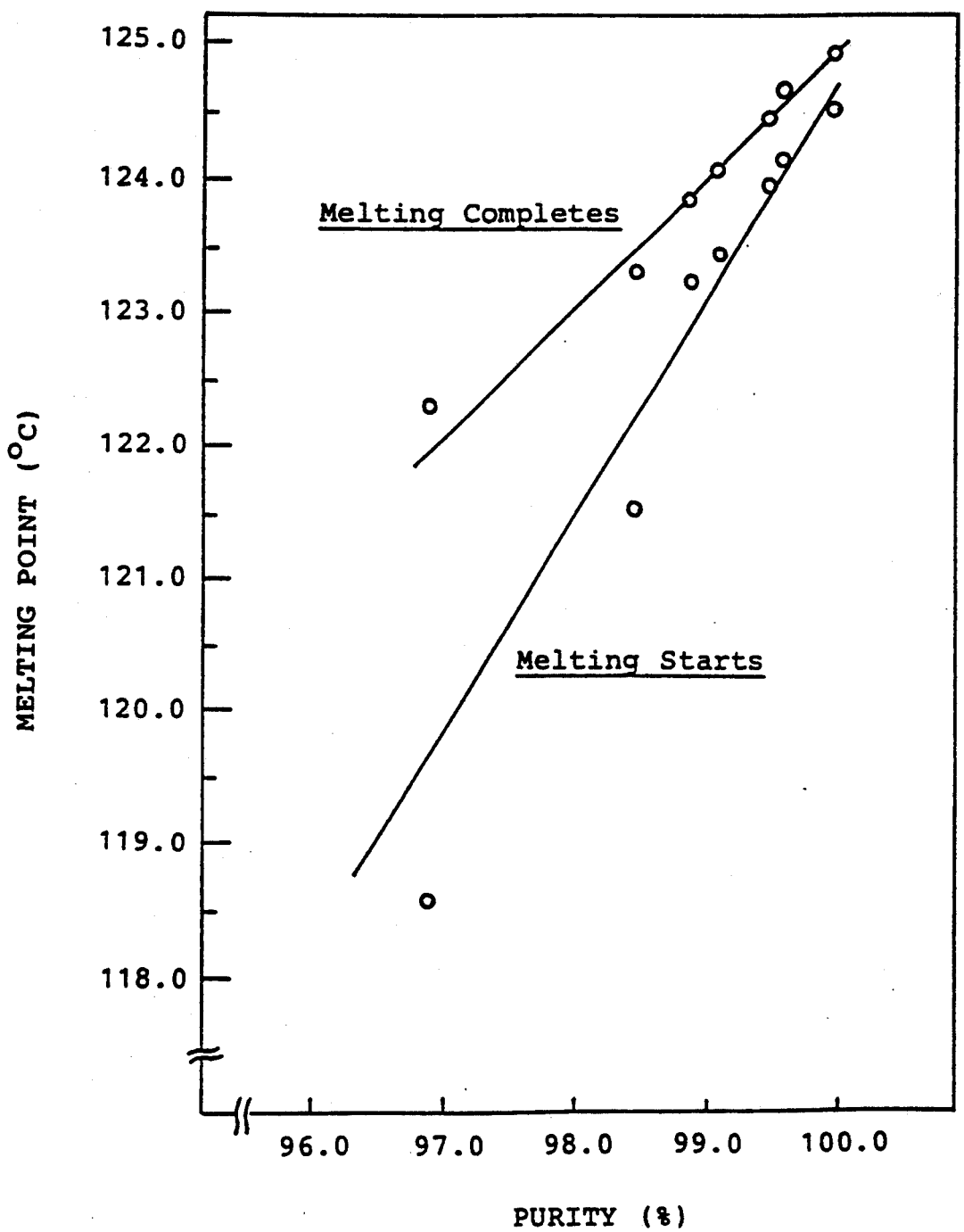

United States Patent [19]
Onoe et al.

[11] Patent Number: 5,175,372
[45] Date of Patent: Dec. 29, 1992

[54] PROCESS OF PRODUCING HIGH PURITY BIS(4-HYDROXYPHENYL)SULFIDES AND HEAT-SENSITIVE RECORDING MATERIALS CONTAINING THE SAME

[75] Inventors: Akira Onoe; Masao Kawamura; Kunioki Kato; Tomiharu Amitani; Makoto Sato; Tsuyoshi Morishita, all of Hyogo, Japan

[73] Assignee: Seitetsu Kagaku Co., Ltd., Hyogo, Japan

[21] Appl. No.: 683,554

[22] Filed: Apr. 10, 1991

Related U.S. Application Data

[62] Division of Ser. No. 365,142, Jun. 12, 1989, Pat. No. 5,102,858.

[30] Foreign Application Priority Data

Jun. 14, 1988 [JP] Japan ................. 63-147157

[51] Int. Cl.$^5$ ............................. C07C 319/14
[52] U.S. Cl. .................................... 568/48
[58] Field of Search ........................ 568/48

[56] References Cited

U.S. PATENT DOCUMENTS

| | | | |
|---|---|---|---|
| 3,390,190 | 6/1968 | Curtis et al. ............ | 568/48 |
| 3,678,115 | 7/1972 | Fujisawa et al. ......... | 568/48 |
| 4,380,671 | 4/1983 | Yamaguchi et al. ....... | 568/48 |

FOREIGN PATENT DOCUMENTS 1213260  8/1989  Japan ................. 568/48

Primary Examiner—Marianne M. Cintins
Assistant Examiner—Margaret J. Argo
Attorney, Agent, or Firm—Wegner, Cantor, Mueller & Player

[57] ABSTRACT

In a process of producing high purity bis(4-hydroxyphenyl)sulfides which comprises reacting phenols with sulfur dichloride in an organic solvent, the improvement comprising: reacting the phenols with sulfur dichloride in a nonpolar organic solvent; removing partly or wholly the nonpolar organic solvent after the reaction; adding a polar organic solvent to the reaction mixture to dissolve the reaction mixture therein at elevated temperatures; and crystallizing out the high purity bis(4-hydroxyphenyl)sulfides.

There is further provided a high performance heat-sensitive recording material which comprises high purity bis(4-hydroxy-3-methylphenyl)sulfide thus prepared and having a melting point in the range of from 123.9° C. to 124.9° C. as a developer and a fluoran compound as a color former.

8 Claims, 1 Drawing Sheet

PROCESS OF PRODUCING HIGH PURITY BIS(4-HYDROXYPHENYL)SULFIDES AND HEAT-SENSITIVE RECORDING MATERIALS CONTAINING THE SAME

This application is a divisional of Ser. No. 07/365,142, filed Jun. 12, 1989, now U.S. Pat. No. 5,102,858.

This invention relates to a process of producing high purity bis(4-hydroxyphenyl)sulfides and heat-sensitive recording materials containing the same.

Heat-sensitive recording materials are composed of electron donating colorable color formers and electron accepting developers. The normally colorless color formers are darkly colored when being put into contact with the electron accepting developers such as phenolic compounds including bisphenol A at elevated temperatures. Such heat-sensitive recording materials have found application in various fields, for example, as facsimile transmission.

However, there is increasing demand of improved heat-sensitive recording materials as they are more widely used. In particular, it is desired that heat-sensitive recording materials turn dark black immediately when being heated and, still they have no fog during use or storage. Further, it is desired that they form color stable in storage, and still they produce no background coloration.

Bis(4-hydroxyphenyl)sulfides are already known as being useful as developers, and heat-sensitive recording materials containing the sulfide having a melting point of 118°–120° C. as developers is described in Japanese Patent Laid-open No. 57-41996. However, it has been found that there takes place a significant degree of background coloration in this prior heat-sensitive recording material, and moreover, they need high temperatures to develope dark color, and are insufficient in heat resistance.

Many methods of producing bis(4-hydroxyphenyl)sulfides are already known. In a method described in U.S. Pat. No. 3,390,190, phenols are reacted with sulfur dichloride in toluene, and the reaction products are recrystallized from a 10% aqueous solution of sodium carbonate, to provide 99% purity bis(4-hydroxyphenyl)sulfides. In Japanese Patent Laid-open No. 51-34134, there is described a further method in which phenols and sulfur dichloride are reacted in cyclohexane which has been saturated with anhydrous hydrogen chloride and contains a small amount of seed crystals of bis(4-hydroxyphenyl)sulfides, and after the reaction the reaction products are treated with sodium hydroxide and ether, to produce high purity bis(4-hydroxyphenyl)sulfides.

However, the bis(4-hydroxyphenyl)sulfides thus prepared by these prior methods have also been found to fail heat-sensitive recording materials as desired as hereinbefore described.

The present inventors have made intensive investigations of heat-sensitive recording materials containing bis(4-hydroxyphenyl)sulfides as developers, and found that insufficient performance of the prior art heat-sensitive recording materials derives substantially from impurities contained in the bis(4-hydroxyphenyl)sulfides used as developers.

There may be mentioned as the impurities, for example, bis(4-hydroxyphenyl)disulfides or bis(4-hydroxyphenyl)sulfides having chlorines at 3- or 3'positions thereof. When the bis(4-hydroxyphenyl)sulfides contain the impurities in significant amounts, the sulfides have lower and wider range of melting points. Namely, the melting starts at low temperatures, and the temperature difference between the start and completion of the melting is large.

Now the use of bis(4-hydroxyphenyl)sulfides having specific ranges of melting points as taken as a measure of purity required as developers together with fluoran compounds as color formers has been found to provide high performance heat-sensitive recording materials as hereinbefore described.

It is, therefore, an object of the invention to provide a process of producing very high purity bis(4-hydroxyphenyl)sulfides in industrially simple manners.

It is a further object of the invention to provide high performance heat-sensitive recording materials containing such high purity bis(4-hydroxyphenyl)sulfides as developers.

In accordance with the invention, there is provided a method of producing high purity bis(4-hydroxyphenyl)sulfides which comprises reacting phenols which have the general formula of

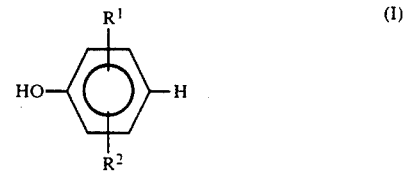

wherein $R^1$ and $R^2$ independently represent a hydrogen or an alkyl of 1-4 carbons, with sulfur dichloride in organic solvents, to provide bis(4-hydroxyphenyl)sulfides having the general formula of

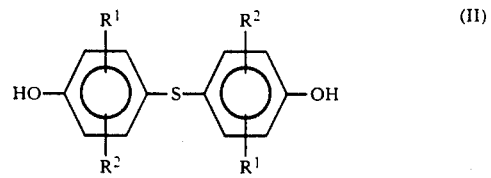

wherein $R^1$ and $R^2$ are the same as before;
the improvement comprising:
(a) reacting the phenols with sulfur dichloride in a nonpolar organic solvent at temperatures ranging from −10° C. to 30° C.;
(b) removing partly or wholly the nonpolar organic solvent by distillation from the resultant reaction mixture after the reaction;
(c) adding a polar organic solvent to the reaction mixture to dissolve the reaction mixture therein at elevated temperatures;
(d) filtering the resulting mixture to remove solid materials at elevated temperatures;
(e) washing the resultant filtrate with an aqueous alkaline solution at elevated temperatures;
(f) separating an organic layer from the filtrate at elevated temperatures; and
(g) cooling the organic layer to crystallize out the bis(4-hydroxyphenyl)sulfides and separating the sulfides.

In the process of the invention, the phenols used are represented by the general formula (I), and include, for example, phenol, o-cresol, 2,6-dimethylphenol, 2,6-diisopropylphenol and 2-t-butylphenol.

The reaction is carried out preferably by first dissolving the phenols in nonpolar organic solvents, and then adding thereto sulfur dichloride gradually, preferably adding dropwise to the solution of the phenols, under cooling and with stirring.

Sulfur dichloride is used in amounts of about 0.9–1.1 moles per two moles of the phenols used usually at temperatures ranging from −10° C. to 30° C., preferably at temperatures of about 0°–20° C. When the reaction temperature is too low, the reaction proceeds infeasibly slowly, whereas when the reaction temperature is too high, undesired side reactions take place so that yield and selectivity of the desired bis(4-hydroxyphenyl)sulfides are low.

The nonpolar organic solvents used are water-immiscible hydrocarbons such as aliphatic, alicyclic and aromatic hydrocarbons. Thus, as such solvents, there may be preferably used hexane, heptane or cyclohexane. Carbon tetrachloride may be also used as nonpolar organic solvents. The nonpolar organic solvents are used usually in amounts of not less than about three times in weight as much as the weight of sulfur dichloride used. When the amount of the solvents used is less than about three times in weight as much as the weight of sulfur dichloride used, the yield and selectivity to produce the desired bis(4-hydroxyphenyl)sulfides are low. However, the use of more than about 20 times the weight of sulfur dichloride little improves the yield and selectivity, and hence it is not desired from the standpoint of process economy.

The resultant bis(4-hydroxyphenyl)sulfides have a small solubility in such nonpolar organic solvents as above mentioned, so that the resultant reaction mixture is a heterogeneous slurry of crystals of the bis(4-hydroxyphenyl)sulfides formed.

The use of polar organic solvents in the reaction is not desired since much amounts of isomeric by-products as well as polysulfides such as di- and trisulfides are produced, and as results no good yield of the desired bis(4-hydroxyphenyl)sulfides is attained.

After the reaction, the nonpolar organic solvents are removed partly or wholly by distillation from the reaction mixture. Then, polar organic solvents are added to the reaction mixture, and the resultant mixture is heated to elevated temperatures to dissolve the formed bis(4-hydroxyphenyl)sulfides therein. The polar organic solvents used are such that the bis(4-hydroxyphenyl)sulfides formed have a large solubility therein, and there may be mentioned as such polar organic solvents, halogenated aromatic or aliphatic hydrocarbons. In particular, chlorobenzene, o-dichlorobenzene, ethylene dichloride, trichloroethylene or perchloroethylene is preferred. The polar organic solvents are used in amounts of about 3–10 times, preferably of about 4–6 times, as much as the weight of the crystals formed in the reaction.

The mixture is usually heated to elevated temperatures of not less than about 70° C. to dissolve at least a substantial amount of the bis(4-hydroxyphenyl)sulfides formed therein. Usually it is not necessary to heat the mixture at temperatures of more than about 100° C.

Then the mixture is filtered at elevated temperatures to remove solid materials, and then washed with an aqueous alkaline solution at elevated temperatures, preferably at temperatures of about 70°–90° C. As the aqueous alkaline solution, aqueous sodium hydroxide or sodium carbonate solution in concentrations of about 1–10% by weight is preferably used.

After the washing, the mixture is separated into an organic layer and an aqueous layer at elevated temperatures, preferably at temperatures of about 60°–90° C. If necessary, the organic layer may be further washed with an aqueous solution of reducing agents such as sodium sulfite or hydrosulfite (sodium dithionite) at elevated temperatures, preferably at temperatures of about 60°–90° C., followed by separation of an organic layer from an aqueous layer at elevated temperatures, preferably at temperatures of about 60°–90° C.

The thus resultant organic layer is then cooled to room temperatures or below, preferably to temperatures of not more than about 20° C., to crystallize out the bis(4-hydroxyphenyl)sulfides, and the crystals are collected by filtration, for example, to provide high purity bis(4-hydroxyphenyl)sulfides, usually of not less than about 99.5% in purity.

As set forth above, in accordance with the invention, high purity bis(4-hydroxyphenyl)sulfides are obtained by a so-called one pot operation without separating crude crystals from the reaction mixture and recrystallizing them from solvents.

As a further aspect of the invention, there is provided in accordance with the invention a heat-sensitive recording material which comprises high purity bis(4-hydroxy-3-methylphenyl)sulfide having a melting point in the range of from 123.9° C. to 124.9° C. (as measured with a Mettler automatic melting point measuring apparatus Model FP 800) as developers and fluoran compounds as color formers.

The above specified high purity bis(4-hydroxy-3-methylphenyl)sulfide has a purity of not less than 99.5% by liquid chromatographic analysis. FIG. 1 illustrates a relationship between the purity and melting point of bis(4-hydroxy-3-methylphenyl)sulfide. As seen, the purer the sulfide, the higher the melting point of the sulfide and the smaller the difference between the temperatures at which the melting of the sulfide starts and completes.

The purity of bis(4-hydroxy-3-methylphenyl)sulfide has a great influence upon background coloration of heat-sensitive recording materials containing the sulfide as developers. More specifically, the use of high purity bis(4-hydroxy-3-methylphenyl)sulfide having a melting point in the range of from 123.9° C. to 124.9° C. together with fluoran compounds as color formers provides a higher performance heat-sensitive recording material which turns dark black substantially immediately at lower temperatures than the conventional heat-sensitive recording materials with substantially no background coloration. When the bis(4-hydroxy-3-methylphenyl)sulfide used has a melting point of smaller than 123.9° C., the resultant heat-sensitive recording material develops color gradually at lower temperatures, to produce background coloration thereon.

The fluoran compound usable in the invention includes, for example, 3-diethylamino-7-(o-chloroanilino)fluoran and 3-dibutylamino-7-(o-chloroanilino)fluoran. A mixture of these may also used.

The heat-sensitive recording material of the invention may be produced in a conventional manner. For instance, at first, aqueous dispersions of the high purity bis(4-hydroxy-3-methylphenyl)sulfide and color formers are separately prepared. In place of aqueous dispersions, organic dispersions in organic solvents in which neither the sulfide nor the color formers are soluble may be prepared, if desired. The dispersions may contain organic binders such as polyvinyl alcohol, carboxymethyl cellulose, methyl cellulose, hydroxyethyl cellulose, styrene-maleic acid copolymer or its salt, diisobutylene-maleic acid copolymer or its salt, sodium alginate, various modified starch, gum arabic, styrene-butadiene latex, terpene resin or cyclized rubber. The dispersions may further contain fillers such as kaolin, talc, titanium oxide, calcium carbonate or zinc oxide, water resistant agents, lubricants such as waxes or fatty acid salts, sensitizers such as p-benzylbiphenyl, surfactants, or defoaming agents, when desired.

The dispersions are then admixed together, coated on a substrate such as paper, and dried, to provide heat-sensitive recording materials. It is preferred that the heat-sensitive recording material of the invention is composed of 1-15 parts by weight of the high purity bis(4-hydroxy-3-methylphenyl)sulfide as developers and 1-10 parts by weight of binders in relation to 1-10 parts by weight of fluoran compounds as color formers.

The invention will now be described more speicifically with reference to examples below.

EXAMPLE A

Production of High Purity Bis(4-hydroxyphenyl)sulfides

Example 1

In a two liter capacity four necked flask provided with a stirrer, a dropping funnel and a thermometer, there were placed 700 g of hexane, and 216.2 g (2 moles) of o-cresol were dissolved therein. An amount of 103.0 g (1 mole) of sulfur dichloride was added to the solution dropwise under stirring at 15° C. After the addition, the reaction was continued for another one hour at 15° C., to provide a white slurry as a reaction mixture containing crystals formed.

After the reaction, hexane was removed by distillation from the reaction mixture, and 1000 g of chlorobenzene were added to the reaction mixture. The resultant mixture was then heated to about 95° C. to dissolve the reaction products therein. Then, the mixture was filtered at 82°-87° C. to remove solid materials therefrom, and washed with a 2% by weight aqueous solution of sodium carbonate at about 80° C.

An organic layer was separated from an aqueous layer at 70°-77° C., and washed with an aqueous solution of hydrosulfite at about 80° C., followed by separation of an organic layer at about 80° C.

Then, the organic layer was cooled to about 20° C., so that bis(4-hydroxy-3-methylphenyl)sulfide crystallized out. The yield was 195.2 g (i.e., 79.0% based on cresol; hereinafter yields are similarly based on the starting phenols used). The sulfide was found to have a melting point of 124.1°-124.6° C. and a purity of 99.6% by liquid chromatographic analysis.

Example 2

An amount of 830 g of cyclohexane was used in place of 700 g of hexane and the reaction was carried out at 10° C., and otherwise in the same manner as in the Example 1, to provide 193.1 g (78.0%) of bis(4-hydroxy-3-methylphenyl)sulfide having a melting point of 124.0°-124.5° C. and a purity of 99.5%.

Example 3

An amount of 730 g of heptane was used in place of 700 g of hexane and otherwise in the same manner as in the Example 1, the reaction was carried out, to provide 194.4 g (78.6%) of bis(4-hydroxy-3-methylphenyl)sulfide having a melting point of 124.1°-124.6° C. and a purity of 99.6%.

Example 4

An amount of 1600 g of carbon tetrachloride was used in place of 700 g of hexane and otherwise in the same manner as in the Example 1, the reaction was carried out, to provide 192.9 g (77.9%) of bis(4-hydroxy-3-methylphenyl)sulfide having a melting point of 123.9°-124.5° C. and a purity of 99.5%.

Example 5

An amount of 188.2 g (2 moles) of phenol was used in place of o-cresol and otherwise in the same manner as in the Example 1, the reaction was carried out, to provide 202.7 g (92.4%) of bis(4-hydroxyphenyl)sulfide having a melting point of 151.2°-152.5° C. and a purity of 99.5%.

Example 6

An amount of 244.3 g (2 moles) of 2,6-dimethylphenol was used in place of o-cresol and otherwise in the same manner as in the Example 1, the reaction was carried out, to provide 213.7 g (77.5%) of bis(3,5-dimethyl-4-hydroxyphenyl)sulfide having a melting point of 142.0°-142.5° C. and a purity of 99.5%.

Example 7

An amount of 356.6 g (2 moles) of 2,6-diisopropylphenol was used in place of o-cresol and otherwise in the same manner as in the Example 1, the reaction was carried out, to provide 296.9 g (76.4%) of bis(3,5-diisopropyl-4-hydroxyphenyl)sulfide having a melting point of 93.5°-94.2° C. and a purity of 99.5%.

Example 8

An amount of 1000 g of o-dichlorobenzene and a 2% by weight aqueous solution of sodium hydroxide were used in place of chlorobenzene and the aqueous solution of sodium carbonate, respectively, and otherwise in the same manner as in the Example 1, the reaction was carried out. An amount of 194.5 g (78.6%) of bis(4-hydroxy-3-methylphenyl)sulfide was obtained, which was found to have a melting point of 124.1°-124.6° C. and a purity of 99.6%.

Example 9

An amount of 1000 g of trichloroethylene was used in place of chlorobenzene, and otherwise in the same manner as in the Example 1, the reaction was carried out, to provide 194.8 g (78.8%) of bis(4-hydroxy-3-methylphenyl)sulfide having a melting point of 124.2°-124.6° C. and a purity of 99.6%.

EXAMPLE B

Heat-Sensitive Recording Materials Using High Purity Bis(4-hydroxy-3-methylphenyl)sulfide

General Procedures

Preparation of Heat-Sensitive Recording Sheet

A mixture of 5 parts (by weight, the same hereinafter) of a color former, 11 parts of p-benzylbiphenyl, 29 parts of a 10% by weight aqueous polyvinyl alcohol solution and 55 parts of water was stirred with a paint conditioner, to prepare a dispersion A. Similarly, a mixture of 15 parts of a developer, 30 parts of a 10% by weight aqueous polyvinyl alcohol solution and 55 parts of water was stirred with a paint conditioner, to prepare a dispersion B.

One part of the dispersion A was admixed with one part of the dispersion B, and the mixture was coated at a rate of 5-6 g/m² (dry amount) on wood free paper, and dried, to provide a heat-sensitive recording sheet.

Reference Example 3

Heat-sensitive recording sheets were prepared by using Crystal violet lactone as color formers, and otherwise in the same manner as in the Example 4.

The performances of the heat-sensitive recording sheets thus prepared are shown in the Table 1.

TABLE 1

| | Temperature (°C.) | | | | | | | | | | Background | Heat- | Saturated |
|---|---|---|---|---|---|---|---|---|---|---|---|---|---|
| | 50 | 60 | 70 | 75 | 80 | 85 | 90 | 100 | 110 | 120 | Coloration | Resistance | Color Darkness |
| Example 1 | 0.05 | 0.05 | 0.07 | 0.10 | 0.50 | 1.25 | 1.26 | 1.30 | 1.30 | 1.30 | 0.05 | 0.07 | 1.30 |
| Example 2 | 0.05 | 0.05 | 0.07 | 0.10 | 0.57 | 1.25 | 1.27 | 1.30 | 1.30 | 1.30 | 0.05 | 0.07 | 1.30 |
| Example 3 | 0.05 | 0.05 | 0.07 | 0.10 | 0.55 | 1.26 | 1.28 | 1.30 | 1.30 | 1.30 | 0.05 | 0.06 | 1.30 |
| Example 4 | 0.06 | 0.06 | 0.06 | 0.06 | 0.09 | 1.00 | 1.24 | 1.28 | 1.30 | 1.30 | 0.06 | 0.06 | 1.31 |
| Reference 1 | 0.25 | 0.26 | 0.32 | 0.40 | 0.86 | 1.25 | 1.27 | 1.30 | 1.30 | 1.30 | 0.25 | 0.29 | 1.31 |
| Reference 2 | 0.19 | 0.20 | 0.24 | 0.29 | 0.55 | 1.25 | 1.26 | 1.30 | 1.30 | 1.30 | 0.19 | 0.22 | 1.30 |
| Reference 3 | 0.11 | 0.12 | 0.15 | 0.38 | 0.69 | 0.94 | 0.98 | 1.12 | 1.21 | 1.22 | 0.11 | 0.78 | 1.25 |

*The figures are color darkness measured by a Macbeth reflux densitometer.

Measurement of Performance of Heat-Sensitive Recording Sheet (1) Temperature Dependence of Color Development Heat-sensitive recording sheets were heated to temperatures ranging from 50° C. to 170° C. under a pressure of 600 g/cm² for a period of 5 seconds by use of a YSS type heat sealer (Tester Sangyo), and then the resultant color density was measured with a Macbeth reflux densitometer at intervals of temperatures.

(2) Background Colorlation

Heat-sensitive recording sheets were left standing at 40° C. for a period of 2 hours, and then at room temperature. Within 30 minutes after the sheets were placed at room temperature, the coloration of the sheet was measured with a Macbeth reflux densitometer.

(3) Saturated Color Darkness

Heat-sensitive recording sheets were heated to 200° C. for a period of 5 seconds by use of the heat sealer, and the coloration of the sheet was measured with a Macbeth reflux densitometer.

(4) Heat-Resistance

Heat-sensitive recording sheets were left standing at 60° C. for a period of 24 hours, and the background coloration of the sheet was measured with a Macbeth reflux densitometer.

Examples 1-3

Heat-sensitive recording sheets were prepared by using high purity bis(4-hydroxy-3-methylphenyl)sulfide of melting points of 123.9°-124.5° C., 124.2°-124.6° C. and 124.5°-124.9° C., respectively, as developers, and 3-dibutylamino-7-(o-chloroanilino)fluoran (TH-107 by Hodogaya Kagaku Kogyo K.K.) as color formers.

Example 4

Heat-sensitive recording sheets were prepared by using high purity bis(4-hydroxy-3-methylphenyl)sulfide of a melting point of 124.2°-124.6° C. as developers, and 3-diethylamino-7-(o-chloroanilino)fluoran (TH-106 by Hodogaya Kagaku Kogyo K.K.) as color formers.

Reference Examples 1 and 2

Heat-sensitive recording sheets were prepared by using bis(4-hydroxy-3-methylphenyl)sulfide of melting points of 118.6°-122.3° C. and 121.5°-123.3° C., respectively, as developers, and 3-dibutylamino-7-(o-chloroanilino)fluoran as color formers.

What is claimed is:

1. In a method of producing high purity bis(4-hydroxy-phenyl)sulfides which comprises reacting phenols which have the general formula of

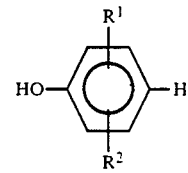

wherein R¹ and R² independently represent a hydrogen or an alkyl of 1-4 carbons, with sulfur dichloride in an organic solvent, to provide bis(4-hydroxyphenyl)sulfides having the general formula of

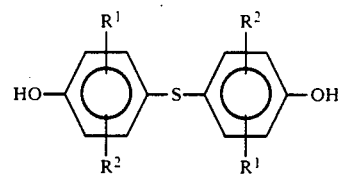

wherein R¹ and R² are the same as before;
the improvement comprising:
(a) reacting the phenols with sulfur dichloride in a nonpolar organic solvent, which is selected from the group consisting of an aliphatic hydrocarbon, an alicyclic hydrocarbon, and carbon tetrachloride, at temperatures ranging from −10° C. to 30° C.;
(b) removing partly or wholly the nonpolar organic solvent by distillation from the resultant reaction mixture after the reaction;
(c) adding a polar organic solvent, which is selected from the group consisting of a halogenated aromatic hydrocarbon and a halogenated aliphatic hydrocarbon, to the reaction mixture to dissolve the reaction mixture therein at temperatures ranging from 70°-100° C.;
(d) filtering the resulting mixture to remove solid materials at temperatures ranging from 70°-90° C.;
(e) washing the resultant filtrate with an aqueous alkaline solution at temperatures ranging from 70°-100° C.;

(f) separating an organic layer from the filtrate at temperatures ranging from 60°–90° C.; and (g) cooling the organic layer to crystallize out the bis(4-hydroxyphenyl)sulfides and separating the sulfides.

2. The method as claimed in claim 1 wherein the nonpolar organic solvent is an aliphatic or alicyclic hydrocarbon.

3. The method as claimed in claim 1 wherein the nonpolar organic solvent is hexane, heptane or cyclohexane.

4. The method as claimed in claim 1 wherein the nonpolar organic solvent is carbon tetrachloride.

5. The method as claimed in claim 1 wherein the polar organic solvent is a chlorinated aliphatic or aromatic hydrocarbon.

6. The method as claimed in claim 1 wherein the halogenated aliphatic hydrocarbon is trichloroethylene.

7. The method as claimed in claim 1 wherein the halogenated aromatic hydrocarbon is chlorobenzene or o-dichlorobenzene.

8. The method as claimed in claim 1 wherein the phenol is phenol, o-cresol, 2,6-dimethylphenol or 2,6-diisopropylphenol.

* * * * *